(12) United States Patent
Iwasaki

(10) Patent No.: US 11,031,193 B2
(45) Date of Patent: Jun. 8, 2021

(54) METHOD FOR MANUFACTURING A TOUCH PANEL

(71) Applicant: FUJITSU COMPONENT LIMITED, Tokyo (JP)

(72) Inventor: Nobuya Iwasaki, Tokyo (JP)

(73) Assignee: FUJITSU COMPONENT LIMITED, Tokyo (JP)

( * ) Notice: Subject to any disclaimer, the term of this patent is extended or adjusted under 35 U.S.C. 154(b) by 184 days.

(21) Appl. No.: 15/800,401

(22) Filed: Nov. 1, 2017

(65) Prior Publication Data

US 2018/0068807 A1 Mar. 8, 2018

Related U.S. Application Data

(62) Division of application No. 13/939,333, filed on Jul. 11, 2013, now Pat. No. 9,837,223.

(30) Foreign Application Priority Data

Aug. 9, 2012 (JP) .............................. JP2012-177297

(51) Int. Cl.
*H01H 9/02* (2006.01)
*H01H 11/00* (2006.01)
(Continued)

(52) U.S. Cl.
CPC .............. *H01H 9/02* (2013.01); *B32B 37/142* (2013.01); *G06F 3/041* (2013.01); *H01H 11/00* (2013.01);
(Continued)

(58) Field of Classification Search
CPC .......... A61M 2207/00; A61M 2207/10; A61M 25/1034; A61M 25/104; B25B 27/10; B29C 65/18; B29C 65/38; B29C 66/1122; B29C 66/5221; B29C 66/63; B29C 66/81463; B29C 66/81881; B29L 2031/7543; B32B 37/0046; B32B 37/06; B32B 37/142; B32B 38/0012; B32B 2457/202;
(Continued)

(56) References Cited

U.S. PATENT DOCUMENTS 9,452,591 B2 * 9/2016 Chung ...................... B32B 7/14
9,870,079 B2 * 1/2018 Kim ........................ G06F 3/041
(Continued)

FOREIGN PATENT DOCUMENTS

JP 2011-113461 6/2011
JP 2011113461 A * 6/2011

OTHER PUBLICATIONS

Patent Abstracts of Japan, Publication No. 2011-113461, Published Jun. 9, 2011.
(Continued)

*Primary Examiner* — Sonya M Sengupta
(74) *Attorney, Agent, or Firm* — Staas & Halsey LLP

(57) ABSTRACT

A method for manufacturing a touch panel includes: adding decoration printing to a sheet member; pasting an adhesive on the sheet member to which the decoration printing is added; forming a non-adhesion film on a position of the adhesive which is opposed to the wiring connected to a body of the touch panel; cutting in a desired shape the sheet member on which the non-adhesion film is formed; and pasting the cut sheet member on the body.

6 Claims, 7 Drawing Sheets

(51) Int. Cl.
*G06F 3/041* (2006.01)
*B25B 27/10* (2006.01)
*A61M 25/10* (2013.01)
*B29C 65/00* (2006.01)
*B29C 65/38* (2006.01)
*B29C 65/18* (2006.01)
*B32B 37/06* (2006.01)
*B29L 31/00* (2006.01)
*B32B 37/00* (2006.01)
*B32B 37/14* (2006.01)
*B32B 38/00* (2006.01)

(52) U.S. Cl.
CPC ..... *A61M 2207/00* (2013.01); *A61M 2207/10* (2013.01); *B29C 66/1122* (2013.01); *B29C 66/63* (2013.01); *B29C 66/81881* (2013.01); *B32B 37/0046* (2013.01); *B32B 37/06* (2013.01); *B32B 38/0012* (2013.01); *B32B 2457/202* (2013.01); *G06F 2203/04103* (2013.01); *Y10T 156/1005* (2015.01); *Y10T 156/1062* (2015.01)

(58) Field of Classification Search
CPC ......... Y10T 156/1005; Y10T 156/1062; G06F 2203/04103; G06F 3/041; H01H 11/00; H01H 9/02
See application file for complete search history.

(56) References Cited

U.S. PATENT DOCUMENTS

| | | |
|---|---|---|
| 2009/0242283 A1 | 10/2009 | Chiu |
| 2010/0013786 A1* | 1/2010 | Nishikawa ............... G06F 3/045 345/173 |
| 2011/0102346 A1 | 5/2011 | Orsley et al. |
| 2011/0195240 A1* | 8/2011 | Inenaga .................. G06F 3/045 428/215 |
| 2011/0199330 A1 | 8/2011 | Hsu et al. |
| 2011/0242057 A1 | 10/2011 | Lee et al. |
| 2011/0298739 A1 | 12/2011 | Wu et al. |
| 2013/0277094 A1* | 10/2013 | Lee ........................ H05K 3/361 174/254 |
| 2014/0054145 A1* | 2/2014 | Chi ........................ H01H 11/00 200/304 |

OTHER PUBLICATIONS

Office Action for U.S. Appl. No. 13/939,333, dated Aug. 13, 2015.
Office Action for U.S. Appl. No. 13/939,333, dated Sep. 8, 2015.
Office Action for U.S. Appl. No. 13/939,333, dated Mar. 10, 2016.
Office Action for U.S. Appl. No. 13/939,333, dated Apr. 22, 2016.
Office Action for U.S. Appl. No. 13/939,333, dated Sep. 29, 2016.
Office Action for U.S. Appl. No. 13/939,333, dated Apr. 4, 2017.
Notice of Allowance for U.S. Appl. No. 13/939,333, dated Sep. 26, 2017.

* cited by examiner

1

FIG. 2A        PRIOR ART
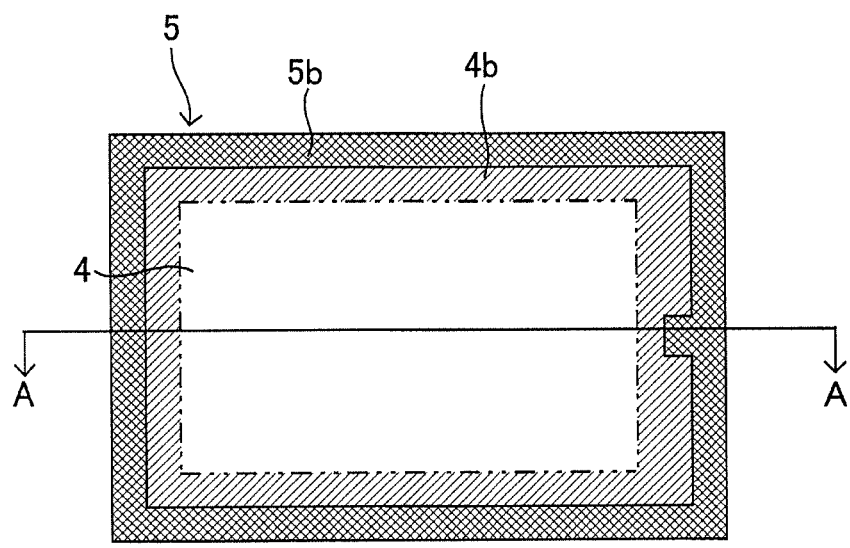
FIG. 2B
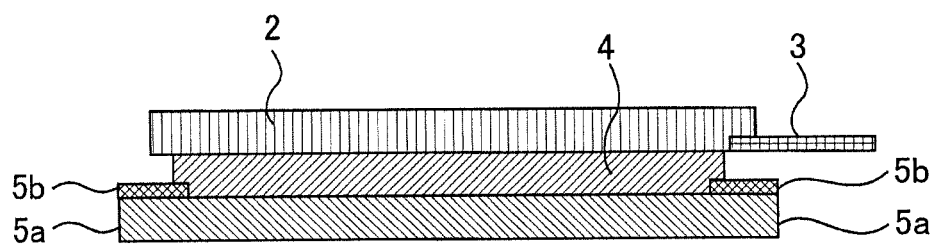

(step S11) DECORATION PRINTING (step S12) PASTE OCA (step S13) FORM NON-ADHESION FILM (step S14) CUT DECORATION FILM (step S15) PASTE DECORATION FILM (step S21) DECORATION PRINTING (step S22) FORM NON-ADHESION FILM (step S23) PASTE OCA (step S24) CUT DECORATION FILM (step S25) PASTE DECORATION FILM

METHOD FOR MANUFACTURING A TOUCH PANEL

CROSS-REFERENCE TO RELATED APPLICATION

This application is a divisional patent application of U.S. patent application Ser. No. 13/939,333 filed on Jul. 11, 2013, now U.S. Pat. No. 9,837,223, which is based upon and claims the benefit of priority of the prior Japanese Patent Application No. 2012-177297 filed on Aug. 9, 2012, the entire contents of which are incorporated herein by reference.

FIELD

A certain aspect of the embodiments is related to a touch panel and a method for manufacturing the same.

BACKGROUND

There has been known a touch panel in which a protective sheet has been pasted on an operation surface thereof (e.g. see Japanese Laid-open Patent Publication No. 2011-113461). To transmit vibration of the touch panel to a user effectively, in the touch panel, a non-adhesion part which is not pasted on the peripheral part of the touch panel is formed on the peripheral part of the protective sheet.

FIG. 1 is an exploded diagram of a conventional touch panel. FIG. 2A is a schematic diagram of the conventional touch panel, as viewed from above. FIG. 2B is a cross-section diagram taken on a line A-A of FIG. 2A. FIG. 2B illustrates a state where the touch panel of FIG. 2A is reversed (i.e., an operation surface is placed at a lowest position).

In FIG. 1, the touch panel 1 includes a touch panel body 2, an FPC (Flexible Printed Circuit) 3 including a wiring for a transparent electrode, an OCA (Optical Clear Adhesive) 4 for pasting a decoration film 5 on the touch panel body 2. The decoration film 5 is for improving a design characteristic of the appearance of the touch panel 1. The decoration film 5 is made of a PET (Polyethylene terephthalate) film 5a, and decoration printing 5b for appearance design is added to a periphery of the PET film 5a.

The OCA 4 has a cut-out portion 4a at a position opposite to the FPC 3, and is not arranged on the FPC 3. This is because, when the OCA 4 has no cut-out portion 4a, in a connection portion 6 (namely, a wiring portion of the FPC 3 connected to the touch panel body 2), the OCA 4 follows unevenness of the connection portion 6 and a flat characteristic of the operation panel (i.e., the decoration film 5) is lost. Moreover, a reason why the OCA 4 is not arranged on the FPC 3 is that the connection portion 6 of the FPC 3 and the decoration film 5 are fixed to the OCA 4 and hence the connection portion 6 can be damaged by the heat contraction of the OCA 4 and the decoration film 5.

FIG. 3 illustrates a method for manufacturing the touch panel 1 indicated by FIGS. 1A, 2A and 2B. As a device for manufacturing the touch panel, a well-known device is used.

First, the decoration printing 5b is added to a periphery of the PET film 5a (step S1). Then, the OCA 4 is processed into a shape as illustrated in FIG. 1 by die cutting processing (step S2). Here, as illustrated in FIGS. 2A and 3, a portion 4b of the OCA 4 corresponding to the connection portion 6 of the FPC 3 and a periphery is removed by the die cutting processing.

Next, the processed OCA 4 is pasted on the PET film 5a to which the decoration printing 5b is added (step S3). Then, the PET film 5a on which the OCA 4 is pasted is cut in a suitable shape (step S4). The cut PET film 5a is pasted on the touch panel body 2 (step S5). It should be noted that a plurality of PET films for touch panel are obtained from the PET film 5a on which the OCA 4 of step S4 is pasted.

SUMMARY

According to an aspect of the present invention, there is provided a touch panel including: a body connected to wiring drawn out to the outside of the touch panel; a sheet member to which decoration printing is added; an adhesive that pastes the sheet member on the body and is the same size as the sheet member; and a non-adhesion film formed between the adhesive and the wiring.

The objects and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 2A is a schematic diagram of the conventional touch panel, as viewed from above;

FIG. 2B is a cross-section diagram taken on a line A-A of FIG. 2A;

DESCRIPTION OF EMBODIMENTS

In the conventional touch panel, since the diecutting processing is necessary for the OCA 4 as described above, the expense for manufacturing a metallic mold for diecutting is required, and hence the manufacturing cost increases. On the other hand, when the diecutting processing is not performed, there is a possibility that the connection portion 6 of the FPC 3 (i.e., the wiring portion of the FPC 3) is damaged as described above.

Hereinafter, a description will be given of embodiments of the present invention with reference to the drawings.

First Embodiment

Figure 1:
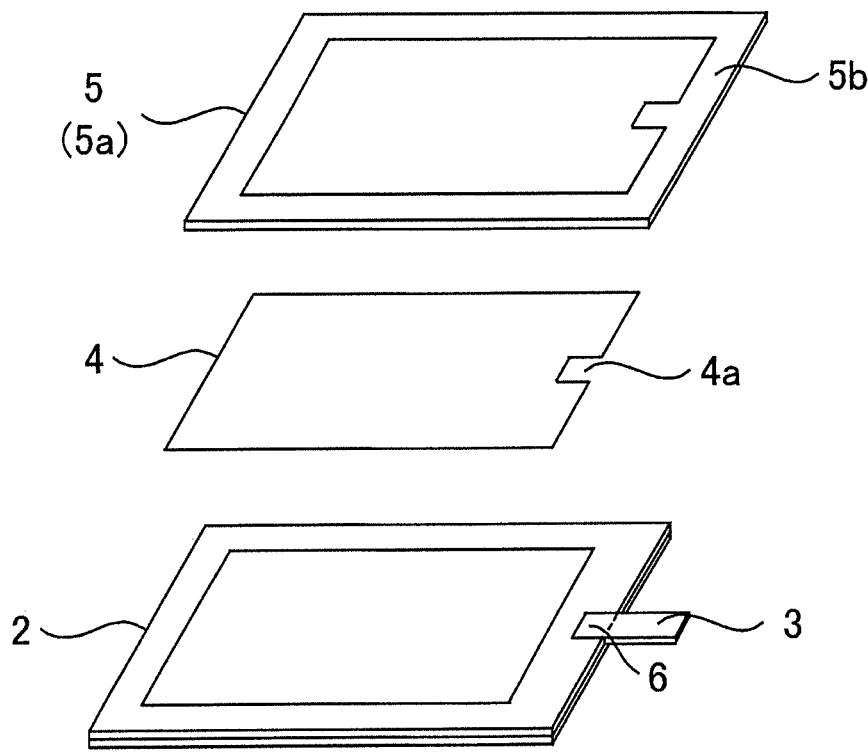
FIG. 1 is an exploded diagram of a conventional touch panel.
Figure 3:
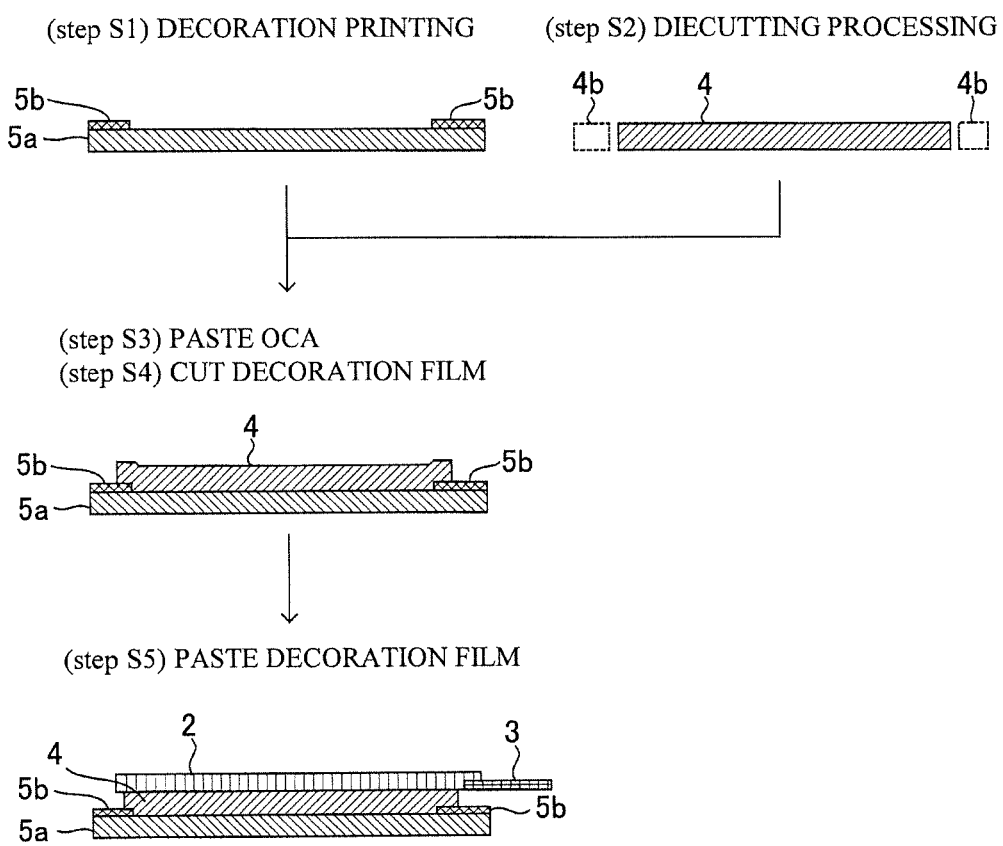
FIG. 3 is a diagram illustrating a method for manufacturing the conventional touch panel.
Figure 4A:
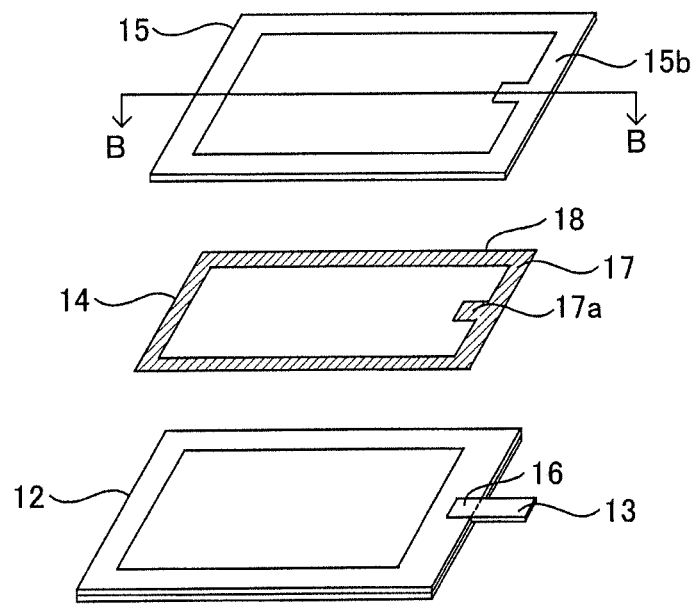
FIG. 4A is an exploded diagram of a touch panel according to a first embodiment.
Figure 4B:
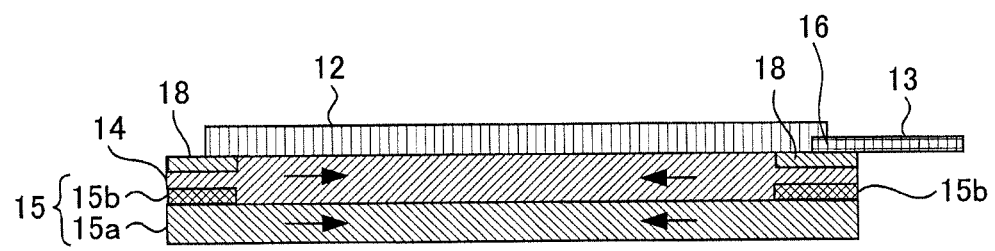
FIG. 4B is a cross-section diagram taken on a line B-B of FIG. 4A.

FIG. 4A is an exploded diagram of a touch panel according to a first embodiment. FIG. 4B is a cross-section diagram taken on a line B-B of FIG. 4A. FIG. 4B illustrates a state where the touch panel of FIG. 4A is reversed (i.e., an operation panel is placed at a lowest position).

In FIG. 4A, a touch panel 11 includes: a well-known resistive film-type or projected capacitive-type touch panel body 12; an FPC (Flexible Printed Circuit) 13 including a wiring for a transparent electrode; an OCA (Optical Clear Adhesive) 14 for pasting a decoration film 15 on the touch panel body 12; and the decoration film 15 for improving a design characteristic of the appearance.

The decoration film 15 is an operation surface for inputting operation against the touch panel body 12, and is made of a PET (Polyethylene terephthalate) film 15a. Decoration printing 15b for appearance design is added to a periphery of the PET film 15a. The decoration film 15 may be made of Polycarbonate or glass, instead of the PET film.

A non-adhesion film 18 is formed on a periphery 17 of the OCA 14 including an area 17a on the OCA 14 which is opposed to a connection portion 16. Thereby, the stress caused by the heat contraction of adhesives or a sheet member is equally applied to the operation surface of the touch panel body 12.

The non-adhesion film 18 is formed by printing an ink containing non-adhesives, such as silicon, on the periphery 17 of the OCA 14, or spraying an ink on the periphery 17 of the OCA 14. The thickness of the non-adhesion film 18, i.e., the thickness of the ink containing non-adhesives is 3 to 5 μm. This is because a minimum thickness is 3 to 5 μm when the ink containing non-adhesives is printed or sprayed using a well-known device. Here, the non-adhesion film 18 may be formed by a film containing non-adhesives, such as silicon. Then, the non-adhesion film 18 is formed on the OCA 14 near the touch panel body 12, as illustrated in FIG. 4B.

The FPC 13 is connected to an end of the touch panel body 12. The connection portion 16 of the FPC 13, i.e., a wiring portion of the FPC 13 connected to the touch panel body 12, contacts the non-adhesion film 18, as illustrated in FIG. 4B. Thereby, even if the stress toward a central direction (e.g. arrows of FIG. 4B) acts on the OCA 14 by the contraction of the decoration film 15, for example, the stress does not act on the connection portion 16 of the FPC 13. Therefore, the connection portion 16 of the FPC 13 won't be damaged by the contraction of the decoration film 15.

Figure 5:
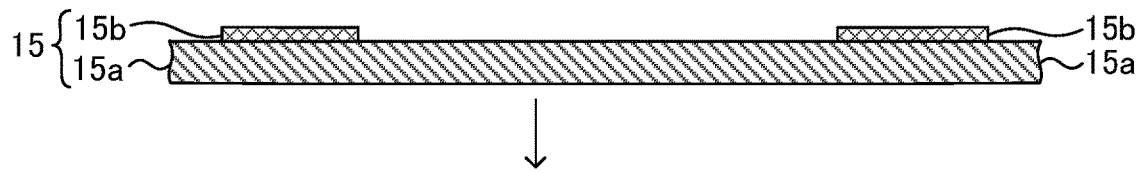
FIG. 5 is a diagram illustrating a method for manufacturing the touch panel according to the first embodiment.
Figure 5:
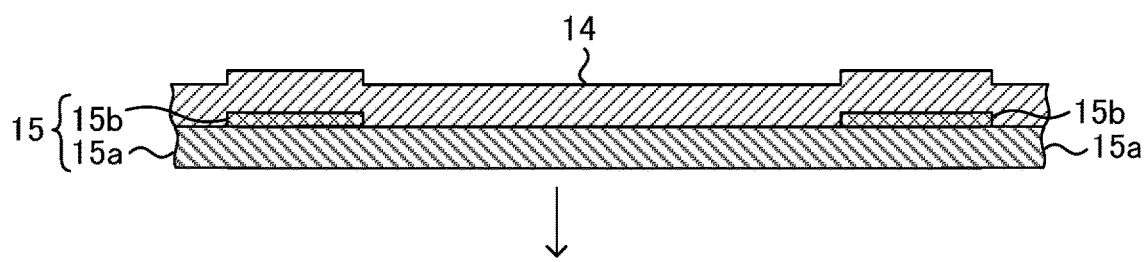
Figure 5:
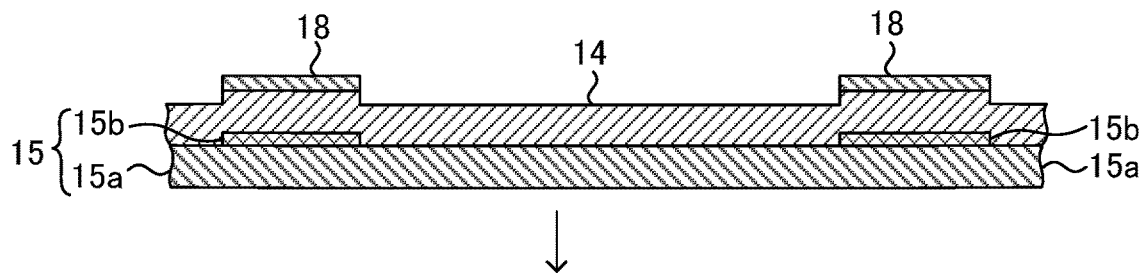
Figure 5:
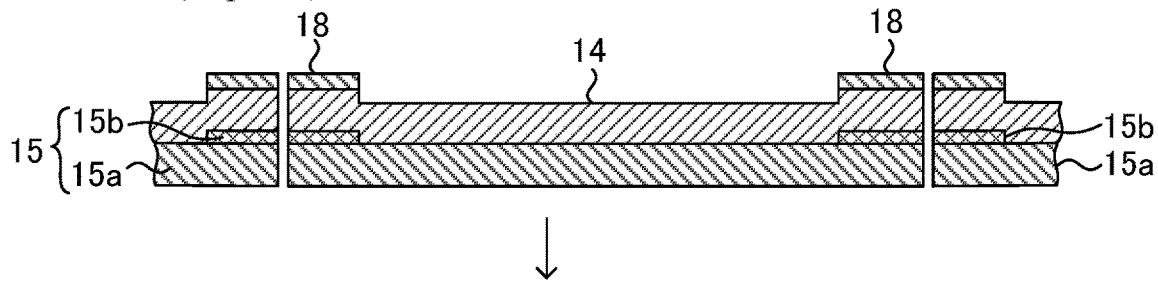
Figure 5:
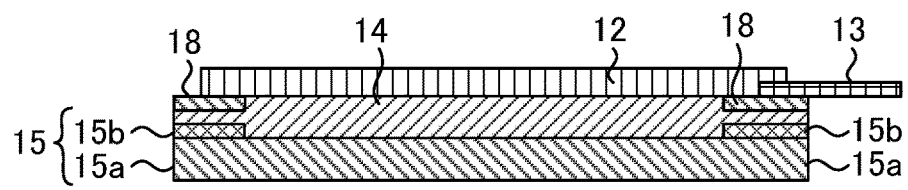

FIG. 5 is a diagram illustrating a method for manufacturing the touch panel 11. As a device for manufacturing the touch panel 11, a well-known device is used.

First, the decoration printing 15b is added to a periphery of the PET film 15a (step S11). Next, the OCA 14 is pasted on the PET film 15a to which the decoration printing 15b was added (step S12). Next, the ink containing the non-adhesives is printed on the periphery 17 of the OCA 14 or sprayed on the periphery 17 of the OCA 14 (step S13). Thereby, the non-adhesion film 18 is formed on the circumference part 17 of the OCA 14.

Then, the PET film 15a on which the OCA 14 is pasted is cut in a desired shape (step S14). Therefore, the OCA 14 is the same size as the PET film 15a in planar view. It should be noted that a plurality of PET films for touch panel are obtained from the PET film 15a on which the OCA 14 is pasted. The desired shape described above is slightly larger than the touch panel body 12. Finally, the cut PET film 15a is pasted on the touch panel body 12 (step S15).

Thus, according to the method for manufacturing the touch panel 11, the diecutting processing of the OCA 14 is unnecessary, and hence the expense for manufacturing the metallic mold for diecutting is not required. Therefore, the manufacturing cost can be reduced, as compared with the method for manufacturing the conventional touch panel. If the diecutting processing of the OCA 14 is performed, it is necessary to paste the OCA 14 on the decoration film 15 with high precision. However, since in the method for manufacturing the touch panel 11 of FIG. 5, the diecutting processing of the OCA 14 is not performed, highly precise pasting is not required, and hence there is a merit that manufacture of the touch panel becomes easy.

As described above, according to the present embodiment, the touch panel 11 includes: the touch panel body 12 connected to the wiring drawn out to the outside of the touch panel, i.e., the FPC 13; the decoration film 15 to which the decoration printing is added; the OCA 14 that pastes the decoration film 15 on the touch panel body 12 and is the same size as the decoration film 15; and the non-adhesion film 18 formed between the OCA 14 and the FPC 13.

Therefore, the wiring of the FPC 13 does not receive the stress according to the heat contraction of the adhesives or the sheet member, so that the damage of the wiring can be avoided. Since the OCA 14 is the same size as the decoration film 15, the metallic mold for diecutting is not required, and hence the manufacturing cost can be reduced.

Moreover, since in touch panel 11, a space is not formed between the decoration film 15 and the touch panel body 12, the problem that a foreign matter adheres to the OCA 14 and the yield of manufacture gets worse is solved. In addition since the non-adhesion film 18 is a thin film formed by printing or spraying, the operation surface, i.e., the flat characteristic of the decoration film 15 is not affected.

Second Embodiment

The present embodiment is different from the first embodiment in a position where the non-adhesion film 18 is formed. Hereinafter, a description will be mainly given of features different from the first embodiment.

Figure 6:
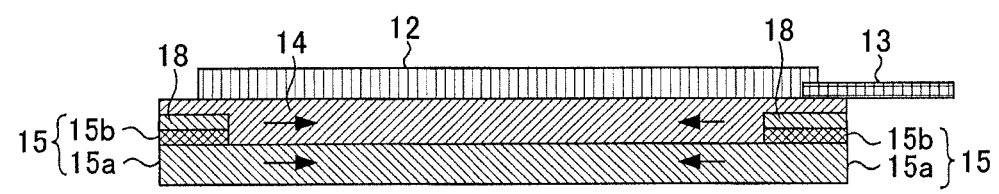
FIG. 6 is a cross-section diagram of the touch panel according to a second embodiment.

FIG. 6 is a cross-section diagram illustrating a variation of the touch panel 11.

The non-adhesion film 18 is formed by printing an ink containing non-adhesives, such as silicon, on the decoration printing 15b, or spraying an ink on the decoration printing 15b. Moreover, the OCA 14 is pasted on the non-adhesion film 18, and the connection portion 16 of the FPC 13 is pasted on the OCA 14. In this case, even if the stress toward a central direction (e.g. arrows of FIG. 6) acts on the OCA 14 by the heat contraction of the decoration film 15, for example, the non-adhesion film 18 functions so as to reduce the stress, and hence the stress rarely acts on the connection portion 16 of the FPC 13. Therefore, it is possible to restrain the connection portion 16 of the FPC 13 from being damaged by the heat contraction of the decoration film 15.

Figure 7:
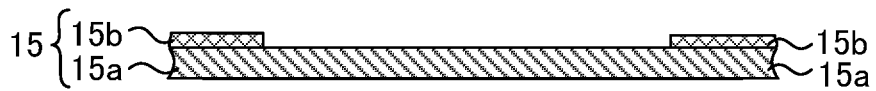
FIG. 7 is a diagram illustrating a method for manufacturing the touch panel according to the second embodiment.
Figure 7:
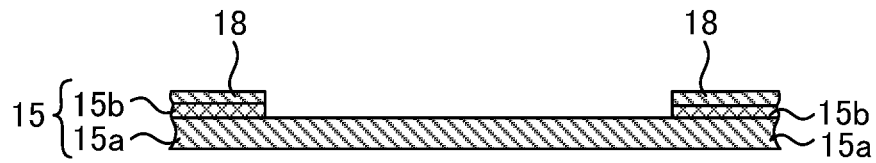
Figure 7:
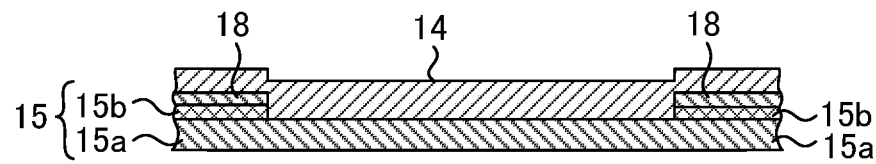
Figure 7:
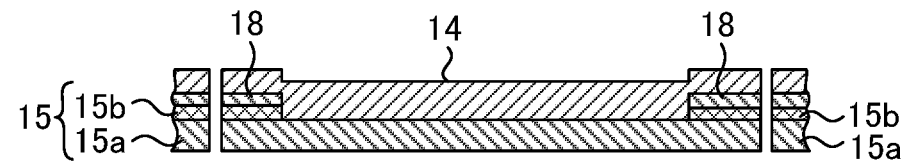
Figure 7:
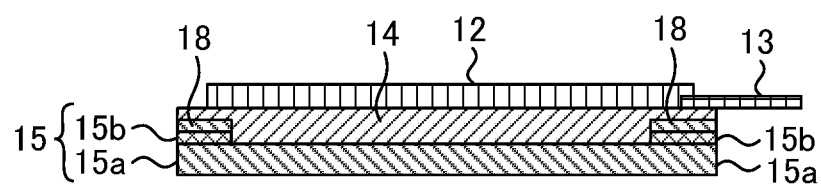

FIG. 7 is a diagram illustrating the method for manufacturing the touch panel 11. As a device for manufacturing the touch panel 11, a well-known device is used.

First, the decoration printing 15b is added to a periphery of the PET film 15a (step S21). Next, the ink containing the non-adhesives is printed on the decoration printing 15b or sprayed on the decoration printing 15b (step S22). Thereby, the non-adhesion film 18 is formed on the decoration printing 15b.

Next, the OCA 14 is pasted on the PET film 15a on which the decoration printing 15b and the non-adhesion film 18 are stacked (step S23). Then, the PET film 15a on which the OCA 14 is pasted is cut in a desired shape (step S24). Therefore, the OCA 14 is the same size as the PET film 15a in planar view. It should be noted that a plurality of PET films for touch panel are obtained from the PET film 15a on which the OCA 14 is pasted. The desired shape described above is slightly larger than the touch panel body 12. Finally, the cut PET film 15a is pasted on the touch panel body 12 (step S25).

As described above, according to the present embodiment, the non-adhesion film 18 is formed between the OCA 14 and the decoration printing 15b. The wiring of the FPC 13 rarely receives the stress according to the heat contraction of the adhesives or the sheet member, so that damage to the wiring can be avoided.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention.

What is claimed is:

1. A method for manufacturing a resistive film-type or projected capacitive-type touch panel comprising:
    adding decoration printing to a sheet member;
    pasting an adhesive on the sheet member to which the decoration printing is added;
    forming a non-adhesion film on a position of the adhesive which is opposed to wiring connected to a body of the resistive film-type or projected capacitive-type touch panel, the non-adhesion film being formed on an outer surface of the body of the resistive film-type or projected capacitive-type touch panel; and
    pasting the sheet member on the body.

2. A method for manufacturing a resistive film-type or projected capacitive-type touch panel comprising:
    adding decoration printing to a sheet member;
    forming a non-adhesion film on the decoration printing which is opposed to wiring connected to a body of the resistive film-type or projected capacitive-type touch panel, the non-adhesion film being formed on an outer surface of the body of the resistive film-type or projected capacitive-type touch panel;
    pasting an adhesive on the sheet member on which the non-adhesion film is formed; and
    pasting the sheet member on the body.

3. The method for manufacturing the touch panel as claimed in claim 1, wherein the non-adhesion film is formed by printing an ink containing non-adhesives on the adhesive, or spraying the ink on the adhesive.

4. The method for manufacturing the touch panel as claimed in claim 2, wherein the non-adhesion film is formed by printing an ink containing non-adhesives on the adhesive, or spraying the ink on the adhesive.

5. The method for manufacturing the touch panel as claimed in claim 1, further comprising:
    cutting the sheet member in a desired shape on which the non-adhesion film is formed;
    wherein the pasting the sheet member on the body includes pasting the cut sheet member on the body.

6. The method for manufacturing the touch panel as claimed in claim 2, further comprising:
    cutting the sheet member in a desired shape on which the adhesive is pasted;
    wherein the pasting the sheet member on the body includes pasting the cut sheet member on the body.

\* \* \* \* \*